United States Patent [19]

Bischofberger et al.

[11] Patent Number: 5,686,629

[45] Date of Patent: Nov. 11, 1997

[54] METHOD AND CYCLIC CARBONATES FOR NUCLEOTIDE ANALOGUES

[75] Inventors: Norbert W. Bischofberger, San Carlos; Kenneth M. Kent, Sunnyvale, both of Calif.

[73] Assignee: Gilead Sciences, Inc., Foster City, Calif.

[21] Appl. No.: 579,499

[22] Filed: Dec. 27, 1995

Related U.S. Application Data

[62] Division of Ser. No. 388,125, Feb. 13, 1995, Pat. No. 5,514,792, which is a continuation of Ser. No. 71,117, Jun. 2, 1993, abandoned.

[51] Int. Cl.⁶ .................. C07D 317/28; C07D 473/34; C07D 317/36; C07D 473/16
[52] U.S. Cl. .................. 549/229; 544/243; 544/244; 544/264; 544/265; 544/267; 544/276; 544/277; 544/309; 544/311; 544/312; 544/314; 544/316; 544/317
[58] Field of Search .................. 549/229

[56] References Cited

U.S. PATENT DOCUMENTS

| | | | |
|---|---|---|---|
| 3,558,656 | 1/1971 | Pfeiffer et al. | 260/340.9 |
| 4,281,125 | 7/1981 | DePompei et al. | 544/224 |
| 4,322,533 | 3/1982 | Lesher et al. | 546/273 |
| 4,563,473 | 1/1986 | Hofman et al. | 546/278 |
| 4,724,233 | 2/1988 | De Clercq et al. | 514/81 |
| 4,808,716 | 2/1989 | Holy et al. | 544/244 |
| 5,142,051 | 8/1992 | Holy et al. | 544/244 |

FOREIGN PATENT DOCUMENTS

| | | |
|---|---|---|
| 61122283 | 6/1986 | Australia. |
| 196865 | 10/1981 | Czechoslovakia. |
| 191656 | 4/1982 | Czechoslovakia. |
| 3723782 | 1/1989 | Germany. |
| 63-056590 | 3/1988 | Japan. |
| 3002206 | 1/1991 | Japan. |

OTHER PUBLICATIONS

Katzhandler, J. et al. *J. Chem. Soc. Perkin Trans. II*, pp. 1729–1739 (1989).
Greene, T.W. et al. *Protective Groups in Organic Synthesis*, pp. 362–368 (1991).
Ichinose, E. et al. *Chemical Abstracts* 115:94511 (1991).
Grahe, G. et al. *Chemical Abstracts* 111:134 129 (1989).
Kawabata, O. et al. *Chemical Abstracts* 109:219655 (1988).
Bronson et al., "Synthesis and Antiviral Activity of Phosphonylmethoxyethyl Derivatives of Purine and Pyrimidine Bases," Nucleotide Analogues 72–87 (1989).
Dodd et al, "Preparation of Glycerols protected at the 2-hydroxy-group and their application to the Synthesis of Lipids," J Am Chem Soc 1(21):2273–2277 (1976).
Foglia et al, "Oxidation of 1–O–(Alk–1–enyl)–2,3Di–O–Acylglycerols: Models for Plasmalogen Oxidation," Lipids 23(5):430–444 (1988).
Gigg et al, "Preparation of Unsymmetrical Diglycerides," J Am Chem Soc 6: 431–434 (1967).
Gomez et al, "Syntheses of D–Glyceraldehyde 2,3–Carbonate, D–Glyceraldehyde 2,3–Diacetate, and Racemic and sn Glyceral 1,2–carbonate," AN QUIM 80(1): 42–44 (1984).
Hirth et al, "Synthesis of Glycery Lether Phosphatides. Part 2. Preparation of 2–O–Acetyl–1–O–[(Z)–9–octadecenyl]–sn–Glyceri 3–Phosphorylcholine (Oleyl–PAF)," HEV CHIM ACTA 66(4):1210–1240 (1983).
Holy et al., "Synthesis of 9–(2–Phosphonylmethoxyethyl)Adenine and Related Compounds," Collect Czech Chem Commun 52:2801–2809 (1987).
Holy et al., "Synthesis of N–(2,3–Dihydroxypropyl) Derivatives of Heterocyclic Bases," Collect Czech Chem Commun 43(8):2054–2061 (1978).
Holy, A., "Synthesis of New Mono–and Disubstituted Hydroxyalkyl and Aminoalkyl Derivatives of Heterocyclic Bases," Collect Czech Chem Commun 43:3444–3465 (1978).
Holy, A., "Synthesis of Racemic and Optically Active erythro–and threo–9(2,3,4–Trihydroxybutyl)Adenines and Related Compounds," Collect Czech Chem Commun 593–612 (1979).
Holy, A., "Synthesis of Some 2,3–Dihydroxypropyl Derivatives of Purine Bases," Collect Czech Chem Commun 3103–3117 (1978).
Juaristi et al., "Use of Hexamethyl Phosphoramide (HMPA) in the Alkylation of Aromatic Amines: Synthesis of Azetidines, Pyrrolidines, Piperidines and Hexahydroazepines,"Tet Lett 45(3):629–636 (1989).
Katzhendler et al, "Conformational Studies of Substituted Five–membered Cyclic Carbonates and Related Compounds by MNDO, and the X–Ray Crystal structure of 4–chlorophenyloxymethyl)–1,3–dioxolan–2–one," J Chem Soc Perkin Trans II 2(11):1729–1739 (1989).
LaMontagne et al., "Preparation of 7–Substituted Pyrrolo[2,3–d]pyrimidines and 9–Substituted Purines as Potential Antiparasitic Agents," J Het Chem 20:295–299 (1983).
Oehlenschlaeger et al., "Synthesis and Mass Spectrometry of 1–Acyl and 3–Acyl –sn–Glyercol Carbonates," Lipids 13(8):557–562 (1978).
Ramaiah, M., "A New Convenient Method for Esterification Using the Ph3P/CC14 System," J Org Chem 50(24):4991–4993 (1985).
Takeuchi et al., "Triazolopyridazin–3–one derivatives," Chem AB 106:5066 (1984).
Tam, W., "Carbonylation of Beta–Aminoethanols, Diols, and Diol Amines," J Org Chem 51(15):2977–1981 (1986).
Ueda, N. et al., "Vinyl Compounds of Nucleic Acid Bases. I. Synthesis of N–Vinyluracil, N–Vinylthymine, and N–Vinyladenine," Die Makromolekulare Chemie 120:13–20 (1968).
Zhelvakova et al, "Lipids. Synthesis of 1,2–Diacyl–sn–Glycerols from D–mannitol Using a Carbonate Protection," Zh Org Khim 6(10):1987–1992 (1970).

*Primary Examiner*—Mukund J. Shah
*Assistant Examiner*—King Lit Wong
*Attorney, Agent, or Firm*—Max D. Hensley

[57] ABSTRACT

An improved method for the preparation of acyclic nucleotide analogues comprises first condensing a cyclic carbonate with a purine or pyrimidine base and then reacting the alkylated base with an activated phosphonate. Novel cyclic carbonates are employed to yield the desired phosphonylmethoxyalkyl nucleotide analogues.

6 Claims, No Drawings

METHOD AND CYCLIC CARBONATES FOR NUCLEOTIDE ANALOGUES

This is a divisional of application Ser. No. 08/388,125, filed on Feb. 13, 1995, now U.S. Pat. No. 5,514,798, which is a continuation of U.S. Ser. No. 08/071,117, filed Jun. 2, 1993, now abandoned.

FIELD OF THE INVENTION

This invention relates to the synthesis of acyclic nucleotide analogues. More particularly, it relates to the preparation of phosphonylmethoxyalkyl-substituted nucleoside bases (hereafter, "nucleotide analogues"), and intermediates therefor.

BACKGROUND OF THE INVENTION

Nucleotide analogues which are synthesized by the novel method of this invention are known per se. They are described for example in U.S. Pat. Nos. 4,659,825 and 5,142,051, WO 92/08686 and EP 269,947, 454,427 and 452,935. Various synthetic routes are known. See for instance U.S. Pat. No. 5,130,427; EP 270,885 and WO 92/02511. These nucleotide analogues are known to possess antiviral activity, e.g., as described in U.S. Pat. No. 4,724,233.

Nucleotide analogues of particular interest are purin-9-yl and pyrimidine-1-yl substituted phosphonylmethoxyalkyl compounds (U.S. Pat. Nos. 5,142,051 and 4,808,716), in particular 9-(phosphonylmethoxyethyl)-substituted bases, especially 9-substituted adenine ("PMEA" and "PME"-type analogues), (3-hydroxy-2-phosphonylmethoxy)propyl-substituted bases, especially 1-substituted cytosine ("HPMPC" and "HPMP"-type analogues and 2-phosphonylmethoxypropyl-substituted bases, "PMP"-type analogues), all of which contain an acyclic linkage between the base and the phosphonate moiety.

A known method for the preparation of PMEA involves the reaction of suitably activated alcohols or akyl halides with salts of adenine, usually in dimethylformamide ("DMF") to yield 9-hydroxyethyladenine. See A. Holy, "Collect. Czech. Chem. Commun." 43:3444 (1978); 44:593 (1979); 43:3103 (1978) and 43:2054 (1978). The amino group of 9-hydroxyethyladenine is blocked (U.S. Pat. No. 4,808,716, column 2, lines 58–66 and Holy et al., "Coll. Czech. Chem. Commun." 52:2801 et seq. [1987]). The protected, alkylated base then is reacted with an alkyl diester of p-toluenesulfonyloxymethanephosphonic acid in the presence of sodium hydride in a dipolar aprotic solvent such as DMF. The product is purified on ion exchange and gel chromatography columns.

Another method for the synthesis of nucleotide analogues of the PME type is described in Martin, ACS Symposium Ser. 401, pp.72–87 (1989). This method involves coupling of the heterocyclic base with a substituted alkyl which bears the phosphonylmethyl ether group. This procedure starts with ring opening of 1,3-dioxolane followed by 3 additional steps and then reaction of the intermediate phosphonate with unprotected adenine. This method, however, produces a mixture of 7- and 9-substituted adenyl compounds. Since these isomers are quite difficult to separate, expensive and exhaustive chromatography steps are required to produce the desired $N^9$ derivative.

Thus, the known synthetic routes to the desired analogues suffer from various disadvantages, including costly starting reagents and the need to conduct complex synthetic procedures.

Accordingly, it is an object of this invention to provide a facile preparative method for the analogues of interest.

It is another object of this invention to dispense with the numerous steps characterizing prior methods and in particular to avoid the need to conduct burdensome and expensive chromatographic procedures.

It is a further object to improve the yields of analogue while minimizing impurities and side-products, e.g. regioisomers such as $N^7$-adenyl.

An additional object is to design a synthetic method which produces only crystalline intermediates and therefore simplifies the procedure.

Another object is to obviate the need to employ dioxolane as a starting material.

Another object is to avoid the need for protection and deprotection of amino groups of nucleoside bases.

A still further object is to improve the economics of the preparation of the analogues.

SUMMARY OF THE INVENTION

The objects of this invention are accomplished by a method comprising (a) reacting a purine or pyrimidine base with a cyclic carbonate of structure I

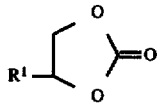

wherein $R^1$ is H; C1–C3 straight or branched alkylene; C2–C6 straight or branched alkenylene or alkynylene; or C1–C2 alkylene substituted with fluoro, azido, amino, $NHR^2$, $N(R^2)_2$ or $OR^3$; and $R^2$ and $R^3$ independently are protecting groups; whereby the base is alkylated, and (b) condensing the alkylated base with a compound of structure II

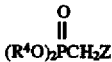

wherein Z is a leaving group and $R^4$ is a protecting group, provided that when the base is adenine then the amino group of adenine is not protected.

The method of this invention employs novel starting materials having structure I wherein $R^1$ is fluoromethylene, azidomethylene, aminomethylene, $CH_2NHR^2$ or $CH_2N(R^2)_2$, wherein $R^2$ independently is a protecting group, and provided that the starting material is substantially stereochemically pure when $R^1$ is fluoromethylene, $CH_2NHR^2$ or $CH_2N(R^2)_2$.

DETAILED DESCRIPTION OF THE INVENTION

The desired nucleotide analogues to be synthesized in accord with the method of this invention typically will have structure III

wherein $R^{11}$ is hydroxyl or a moiety convertible to hydroxyl; $R^1$ is defined above, and B is a purine or pyrimidine base. The hydrolyzable moiety typically is —$OR^4$ wherein $R^4$ is a protecting group.

STARTING MATERIALS

The initial step in the novel method of this invention entails reacting an appropriate cyclic carbonate with a purine or pyrimidine base, their isosteres such as aza or deaza derivatives, and substitutional analogues thereof (hereafter collectively "purine or pyrimidine base"). Various such bases have been described heretofore for inclusion in the desired nucleotide analogues. Thus, the selection of heterocyclic base is driven solely by the desired base component in the product and is not critical for the practice of this method.

For example, the nucleotide analogues of EP 454,427 employ pyrimidine bases of the general formula IV:

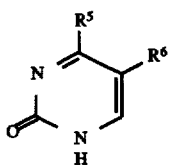
IV wherein $R^5$ is hydrogen, hydroxylamino, hydrazino, alkoxy, amino or substituted amino and $R^6$ is a hydrogen or halogen atom or an alkyl (C1–C3) group, or of the general formula V:

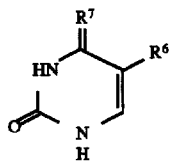
V wherein $R^6$ is as in formula IV and $R^7$ is an atom of oxygen or sulphur, as well as their synthetic analogues such as aza (5-aza, 6-aza) or deaza (3-deaza) derivatives.

Suitable purine bases disclosed for use with the nucleotide analogues of EP 454,427 include natural bases such as adenine, hypoxanthine, guanine, xanthine, and purine derivatives of structure VI:

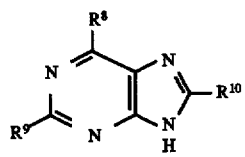
VI wherein $R^8$ and $R^9$ independently are hydrogen, halogen, amino, hydrazino, hydroxylamino, azido, substituted amino, hydroxy, alkoxy, mercapto, alkylmercapto, an alkyl group with a short carbon chain (C1–C4), and combinations thereof, and $R^{10}$ is hydrogen, halogen, hydroxy, alkoxy, mercapto, alkyl-thio, amino or substituted amino, and synthetic analogues, such as aza (2-aza, 8-aza) or deaza (1-deaza, 3-deaza or 7-deaza) derivatives (purine numbering).

In addition, see U.S. Ser. No. 07/925,610 regarding heterocyclic bases for use in PMP-type analogues.

Exemplary purine bases (and their ultimate sites of substitution with a methoxyphosphonylalkyl or methoxyphosphonyl substituted alkyl moiety) are set forth in Table 1.

TABLE 1

| Substituent Designation | Substituent |
|---|---|
| 1 | adenin-9-yl |
| 2 | guanin-9-yl |
| 3 | hypoxanthin-9-yl |
| 4 | purin-9-yl |
| 5 | xanthin-9-yl |
| 6 | 1-deazaadenin-9-yl |
| 7 | $N^2$-benzoylguanin-9-yl |
| 8 | 2-aminopurin-9-yl |
| 9 | 2-amino-6-chloropurin-9-yl |
| 10 | 2-amino-6-thiopurin-yl |
| 11 | 2-amino-6-azidopurin-9-yl |
| 12 | 2,6-diaminopurin-9-yl |
| 13 | 2-chloroadenin-9-yl |
| 14 | 2-methyladenin-9-yl |
| 15 | 2-methylthioadenin-9-yl |
| 16 | 3-deazaadenin-9-yl |
| 17 | $N^6$-dimethyladenin-9-yl |
| 18 | $N^6$-benzoyladenin-9-yl |
| 19 | 6-chloropurin-9-yl |
| 20 | 6-hydrazinopurin-9-yl |
| 21 | 6-hydroxylpurin-9-yl |
| 22 | 6-hydroxylaminopurin-9-yl |
| 23 | 6-methylpurin-9-yl |
| 24 | 6-thiopurin-9-yl |
| 25 | 7-deaza-8-azaadenin-9-yl |
| 26 | 7-deaza-8-azahypoxanthin-9-yl |
| 27 | 8-azaadenin-9-yl |
| 28 | 8-bromoadenin-9-yl |
| 29 | 8-hydroxyadenin-9-yl |

Exemplary pyrimidine bases are set forth in Table 2.

TABLE 2

| Substituent Designation | Substituent |
|---|---|
| 30 | cytosin-1-yl |
| 31 | thymin-1-yl |
| 32 | uracil-1-yl |
| 33 | 4-O-methylthymin-1-yl |
| 34 | 5-methylcytosin-1-yl |
| 35 | 5-halocytosin-1-yl |
| 36 | 6-azacytosin-1-yl |

Ordinarily, the heterocyclic bases will not include uracil-1-yl, thymin-1-yl or hypoxanthin-9-yl. The purine or pyrimidine base typically is selected from the group of guanin-9-yl, 2,6-diaminopurin-9-yl, and adenin-9-yl for PME-type analogues and cytosin-1-yl for HPMP-type analogues.

Exemplary analogues are set forth in Table 3.

TABLE 3

| $R^1$ | Preferred Configuration | Base Designation* |
|---|---|---|
| —CH=CH$_2$ | S | 2, 30 |
| —CH$_2$NH$_2$ | R | 2 |
| —CH$_2$N$_3$ | S | 2, 9, 30 |
| —(CH$_2$)$_2$N$_3$ | R | 2, 9, 30 |
| —CH$_3$ | R | 1, 2, 10, 11, 12, 16, 21, 19, 27 |
| | — | 1, 2, 3, 12, 28, 4, 23, 20, 8, 26, 25 |
| —CH$_2$F | S | 1, 2, 3, 5, 11, 12, 16, 9, 18 |
| —CH$_2$OH | S | 1, 4, 5, 3, 2, 13, 12, 6, 27, 25, 28, 16, 14, 15, 17, 29, 24, 28, 30, 20, 8, 18, 7 |

*See Tables 1 and 2

The compounds of Table 3 are made by the method of this invention using as initial starting materials the designated heterocyclic base and a cyclic carbonate having the appropriate $R^1$ group and stereochemical properties.

CYCLIC CARBONATES

The cyclic carbonate is chosen so as to produce an alkylated base intermediate suitable for ultimate conversion to the desired therapeutic nucleotide analogue, as will be apparent to the ordinary artisan.

For example, synthesis of the N-(3-fluoro-2-phosphonylmethoxypropyl) nucleotide analogues disclosed in EP 454,427 employs a cyclic carbonate of structure I in which $R^1$ is $-CH_2F$.

In the case of the analogues disclosed in WO 92/08686, a cyclic carbonate of structure I is used wherein $R^1$ for example is $-CH_2N_3$, $-CH_2CH_2N_3$, $-CH_2N(R^2)_2$, $-(CH_2)_2N(R^2)_2$, $-CH_2NHR^2$, $-(CH_2)_2NHR^2$, $-CH=CH_2$, $-CH_2CH=CH_2$, $-CH=CHCH_3$, $-C(CH_3)=CH_2$, $-CH=CHCH_2CH_3$, $-CH_2-CH=CH_2$, $-C(CH_3)=CH-CH_3$, $-CH=CH-CH_2-CH_2CH_3$, $-CH=CH-CH(CH_3)-CH_3$, $-CH_2-C(CH_3)=CH-CH_3$, $-CH_2-CH=CH-CH_2-CH_3$, $-CH(CH_3)-CH=CH-CH_3$, $-CH_2-CH_2-CH_2-CH=CH_2$, $-CH(CH_3)-CH_2-CH=CH_2$, $-CH_2-CH(CH_3)-CH=CH_2$, $-C(C_2H_5)=CH-CH_3$, $-CH_2-CH=CH-CH_2CH_2CH_3$, $-CH_2-CH_2-CH_2-CH=CH-CH_3$, $-C\equiv CH$, $-C\equiv C-CH_3$, $-CH-C\equiv CH$, $-CH_2-C\equiv C-CH_3$, $-CH_2-CH_2-C\equiv CH$, $-CH(CH_3)-C\equiv CH$, $-C\equiv C-CH_2-CH_2-CH_3$, $-CH_2-C\equiv C-CH_2CH_3$, $-CH_2-CH_2-CH_2-C\equiv CH$, $-C\equiv C-CH(CH_3)-CH_3$, $-CH(CH_3)-C\equiv C-CH_3$, $-CH(C_2H_4)-CH_2-C\equiv CH$, $-C\equiv C-CH_2-CH_2-CH_2-CH_3$, $-CH_2-C\equiv C-CH_2-CH_2-CH_3$, $-CH(CH_3)-C\equiv C-CH_2-CH_3$, or $-CH_2-C\equiv C-CH(CH_3)(CH_3)$.

Compounds of the PMP, HPMP and PME type are produced from the cyclic carbonates of structure I in which $R^1$ is respectively $-CH_3$, $-CH_2OR^3$ and H.

The nucleotide analogues resulting from the practice of the method of this invention generally will contain a chiral center (Table 3). Either the R or S enantiomer of the carbonate, or less desirably a mixture of R and S enantiomers, may be employed as appropriate to yield the desired enantiomer. The stereoisomerism of the optically active carbonate starting material is maintained through the process of this invention, resulting in the chirally pure or racemic product depending upon the stereochemistry of the starting cyclic carbonate. Thus, for example, when preparing analogues of the PMP-type one typically will use a cyclic carbonate in the R configuration. It will be understood that the designation of configuration may change depending upon modifications made during the synthetic process. For example selection of a particular blocking group $R^3$ for the hydroxymethyl group $R^1$ may change the designation from R to S with respect to the intermediate or carbonate in question. In general, however, the cyclic carbonates will have the structure VII:

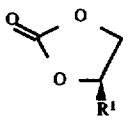
VII wherein $R^1$ is H; C1–C3 straight or branched alkylene; C2–C6 straight or branched alkenylene or alkynylene; or C1–C2 alkylene substituted with fluoro, azido, amino, $NHR^2$, $N(R^2)_2$ or $OR^3$; and $R^2$ and $R^3$ independently are protecting groups. The carbonate VII will be present in compositions which are substantial optically pure as to the carbonate.

Suitable starting cyclic carbonates are commercially available (racemic methyl and optically pure vinyl substituents) or are synthesized from commercially available starting materials in accord with methods know per se in the art. For racemic carbonates where $R^1$ is C1 fluoroalkylene, see Katzenbendler, et. al., *J. Chem. Soc. Perkin Trans*, (1989) 2(11):1729–1739. However, the stereochemically pure fluoroalkylene enantiomers (R or S, substantially free of the other isomer) are novel. For example, they can be produced from chirally pure choropropanediol, which is converted to 1,2-dihydroxy-3 fluoropropane, or from glycidol reacted with a fluoride source such as NaF or KF to produce the same intermediate. The carbonate is obtained by cyclizing the diol using conventional procedures. Other methods starting from chirally pure reactants will be apparent to the artisan. In addition, the enantiomers can be obtained from racemic mixtures by optical resolution chromatography.

Hydroxymethyl carbonates are known as racemates (Czech patent CS 191656B, 1982), and may be obtained in optically pure form using optically resolved solketal as starting material (Jpn Kokai 61122283, Jun. 10, 1986). See also Gomez, S. et. al., *An. Quim., Ser. C.* (1984) 80(1): 42–44; Pfeiffer, et. al., FR 2006535, 1969; and Gigg, et. al., *J. Chem. Soc. Sec. C* (1967) 6:431–434. The S isomer of trityl protected hydroxymethyl carbonates is used to make the preferred nucleotide analogue S isomer.

Amino and azido methyl carbonates described herein are novel, as are their stereochemically pure enantiomers. These also are produced by cyclization of the appropriate diol. The stereochemically pure enantiomers of the protected aminomethyl carbonates ($NHR^2$ or $N[R^2]_2$) are novel and also may be produced by cyclization of the diol.

PROTECTING GROUPS

The protecting groups are used to confer base stability on the intermediates. The protecting groups $R^2$ and $R^3$ are capable of being removed to generate the free amino or hydroxyl groups. Among the protecting groups $R^2$ are for example acyl, benzoyl, isobutyryl, or triphenylmethyl; $R^3$ is chosen from a wide variety of substituents, and includes triphenylmethyl, trialkylsilyl, benzyl and methoxymethyl; and $R^4$ is for example C1–C8 straight or branched chain alkyl, aryl, aralkyl, cycloalkyl, trialkylsilyl, arylalkylsilyl and the like. The selection of protecting group is not critical and need only be guided by the efficacy of the group in preventing reaction at the protected site and the facility of subsequent removal of the protecting group as may be desired. Examples of suitable protecting groups $R^2$ and $R^3$, and their use, are disclosed by Greene, "Protective Groups in Organic Synthesis" pp 14–50 (Groups 1–54) and 218–287.

ALKYLATION OF BASE

The purine or pyrimidine base is condensed with the cyclic carbonate by heating the two starting materials in the presence of catalytic base and a suitable solvent at sufficiently high temperature (typically 120°–125° C.) and time to achieve alkylation of a heterocyclic nitrogen atom. Suitable solvents for this reaction include aprotic dipolar solvents such as DMF, N-methylpyrrolidone and DMSO.

The catalytic base generally is inorganic and preferably is NaOH, but other bases such as potassium carbonate, KOH, KOtBu, or cesium carbonate may be satisfactory.

The alkylated intermediate shown in structure VIII is recovered easily by cooling the reaction mixture to about 0° C. and adding a substantially nonpolar (relative to DMF) organic solvent, such as ethyl acetate, ether, ethanol, methanol, xylene or toluene, to induce precipitation of the crystalline intermediate, although other conventional methods can be employed to recover the product. Structure VIII is depicted below:

VIII wherein $R^1$ and B are defined above.

Interestingly, when the heterocyclic base B in structure VIII is adenyl or an adenyl derivative, the reaction is specific for the primary carbon of the cyclic carbonate, i.e., the heterocyclic base attacks the unsubstituted primary methylene group of I virtually quantitatively. Further, adenine and its analogues are alkylated substantially only at $N^9$, thereby obviating the need to separate regioisomers.

PHOSPHONYLMETHOXY SUBSTITUTION

The next step involves the addition of the alkylated heterocyclic intermediate of structure VIII to an activated methylphosphonate derivative of structure II in the presence of a suitable base and an aprotic polar solvent such as DMF or pyridine. If unprotected hydroxymethyl carbonate was used in the preceding step, the hydroxymethyl group will be protected before participation in this reaction. The leaving group Z of structure II usually is halogen or a sulfonate ester. Exemplary compounds of structure II include diethyl trifluoromethylsufonyloxymethyl phosphonate or diethyl toluenesulfonyloxymethyl phosphonate. The reaction of compounds of structure II with those of VIII is conducted under cooling conditions, typically 0 degrees C., until the product of structure III is obtained (about 1-2 hours). The reaction then may be quenched with weak acid and the product recovered using standard work-up procedures such as extraction, chromatography, crystallization or the like. An advantage of this method, however, is that chromatography is not required, particularly for the readily crystallized phosphonate diesters.

An advantage of the method of this invention is that it is not necessary to protect purine amino groups, e.g. with benzoyl or the like, prior to reacting the derivatized purine of structure VIII with the structure II phosphonate. This greatly simplifies the purification and recovery of the products, enhances yield and reduces cost. However, if desired, the amino and/or any labile groups of the purine or pyrimidine base nay be protected using conventional substituents.

DEPROTECTION

An optional step is the deprotection of the phosphonylmethoxyalkyl purine or pyrimidine whereby the $R^2$, $R^3$ and/or $R^5$ substituents are replaced by hydrogen. This typically includes deprotecting the phosphonate to remove the $R^4$ protecting groups, deprotecting blocked alkylamino groups, or removing the $R^3$ protecting groups in the preparation of HPMP-type nucleotide analogues. However, it nay be desirable to leave certain of the $R^4$ groups in place, e.g., if the phosphonate ester is intended for use as a prodrug.

The protecting groups should be removed after the addition of the phosphonylmethoxy moiety. $R^2$ or $R^3$ on the one hand, and $R^4$ on the other, optionally are selected so that $R^3$ or $R^2$ are deprotected in preference to $R^4$.

Deprotection is accomplished using standard chemistries, for example, reaction with bromotrimethylsilane or trimethytsilyliodide, or an acid such as HBr, HI or TFA.

The following examples are illustrative only and are not to be construed as limiting the scope of the invention. All citations are expressly incorporated by reference.

EXAMPLE 1

A. Diethyl p-toluenesulfonyloxymethylphosphonate

A mixuture of diethyl phosphite (700 g, 5.07 mmole), paraformaldehyde (190 g, 6.33 mole) and triethylamine (51.0 g, 0.50 mole) in toluene (2.8 L) is heated ca 2 hr at 85°-90° C., then under relux for ca 1 h. The resulting solution is cooled to ca. 0° C., and checked by NMR ($CDCl_3$) for completion of the reaction (in-process control). Then p-toluenesulfonyl chloride (869 g, 4.56 mole) and triethylamine (718 g, 7.09 mole) are added with cooling (0°-10° C.). The resulting mixture is stirred at ca. 22° C. for 17-24 h and checked by NMR ($CDCl_3$) for completion of the reaction (in-process control). The solids are removed by vacuum filtration. The filtrate is washed with water (2×) and dried over anhydrous magnesium sulfate. The solvent is evaporated in vacuo to give the title compound as an oil in 65-75% (1060-1225 g) yield. As an in-process control, NMR ($CDCl_3$) is obtained and the product purity is assayed by HPLC [$C_{18}$-35% $C_3CN$ in $KH_2PO_4$ (0.02M)]. The purity of the product is typically 85-95%.

B. 9-(2-Hydroxyethyl)adenine

Adenine (9.1 g), ethylene carbonate (6.0 g), and sodium hydroxide (0.14 g) in DMF (68 ml) were heated at reflux for 2 hr. The solution was cooled to 0°, then 70 ml of toluene were added. After sitting for 2 hr at 0°, the precipitate was collected, rinsed with 100 ml of toluene, then cold ethanol, and dried to afford $N^9$-hydroxyethyladenine.

C. 9-(2-Diethylphosphonylmethoxyethyl)adenine

Sodium hydride (60% oil dispersion, 1.20 g, 30 mM) was added with stirring to a 0°, suspension of 9-(2-hydroxy) ethyladenine (1.79 g, 10 mM) in anhydrous DMF 15 mL). After stirring at 0° for an additional 10-15 minutes, this solution was added over 10-15 minutes to a solution of crude diethyltoluenesulfonyloxymethylphosphonate (4.83 g, ~12 mM) in DMF (10 mL) at 0°. Stirring was continued at 0° for 30-45 minutes at which time TLC ($CH_3OH/CH_2Cl_2$, 15:85) showed the reaction to be complete. The reaction was quenched by careful addition of 80% acetic acid (2.4 mL, 33.4 mM) bringing the pH to 5.5-6.0. After evaporation of the solvents in vacuo, the residue was dissolved in a minimum of hot water (~15-20 mL), allowed to cool to RT, and then extracted with 2×100 mL of hexane (discarded). The aqueous phase was then extracted with 3×100 mL of $CH_2Cl_2$. The $CH_2Cl_2$ extracts were combined and concentrated in vacuo to a semisolid which was crystallized from a minimum volume of hot acetone (~50 mL). A second crop was obtained by evaporating to dryness the acetone filtrate from the first crop, dissolving the residue in $H_2O$ (50 mL) and extracting with 2×50 mL of $CH_2Cl_2$. The $CH_2Cl_2$ extracts were combined and back-extracted with 2×25 mL of $H_2O$. All aqueous phases were combined and concentrated in vacuo to a semisolid which was crystallized from a minimum of ethyl acetate (~10-15 mL).

D. 9-(2-Phosphonylmethoxyethyl)adenine

Bromotrimethylsilane (1.5 mL, 12 mM) was added to a solution of 9-(2-diethylphosphonylmethoxy)ethyladenine (1.0 g, 3.0 mM) in DMF (5.0 mL) and left at 21° for 4 hr. The solution was concentrated in vacuo to a semisolid which was co-evaporated twice with ~5 ml portions of water. The resulting, fine white powder was taken in 2 mL of water and brought to pH ~8 with 2N NaOH causing dissolution. The solution was washed with an equal volume of ethyl acetate, filtered, and acidified with hydrochloric acid (pH 3) inducing pure title compound to precipitate. The precipitate was collected by filtration, rinsed with water and acetone, then dried.

EXAMPLE 2

Synthesis of PMEDAP [9-(2-phosphonylmethoxyethyl)-2,6-diamino-purine]

The method of Example 1 is followed except that 2,6-diaminopurine is substituted for adenine.

EXAMPLE 3

Synthesis of (R)-PMPA and (S)-PMPDAP [(R)-9-(2-Phosphonylmethoxypropyl)adenine and (S)-9-(2-phosphonylmethoxypropyl)-2,6-diaminopurine]

The methods of Examples 1 and 2 are followed as appropriate except that the carbonate has structure VII in which $R^1$ is methyl. The carbonate then is employed in the procedure of Example 1.

EXAMPLE 4

Synthesis of (S)-HPMPC

The method of Example 1 is followed except that $R^1$=—$OR^3$ where $R^3$ is triphenylmethyl and the base is cytosine.

We claim:

1. A compound having the structure I

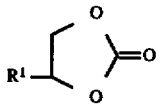

wherein $R^1$ is —$CH_2N_3$, —$(CH_2)_2N_3$, or —$CH_2NH_2$.

2. The compound of claim 1 wherein $R^1$ is azidomethylene.

3. A substantially optically pure compound of claim 1.

4. The compound of claim 1 wherein $R^1$ is aminomethyl.

5. The compound of claim 3 which is the S isomer.

6. The compound of claim 1 which is the R isomer.

* * * * *